United States Patent [19]

Deneke et al.

[11] Patent Number: 4,923,796
[45] Date of Patent: May 8, 1990

[54] METHOD FOR THE QUANTITATIVE ENZYMATIC DETERMINATION OF ADP

[75] Inventors: Ulfert Deneke, Peissenberg; Gerhard Michar; Hans-Otto Beutler, both of Tutzing, all of Fed. Rep. of Germany

[73] Assignee: Boehringer Mannheim GmbH, Mannheim, Fed. Rep. of Germany

[21] Appl. No.: 298,768

[22] Filed: Jan. 17, 1989

Related U.S. Application Data

[63] Continuation of Ser. No. 614,372, May 24, 1984, abandoned, which is a continuation of Ser. No. 59,366, Jul. 20, 1979, abandoned.

[30] Foreign Application Priority Data

Aug. 8, 1978 [DE] Fed. Rep. of Germany ....... 2834704

[51] Int. Cl.$^5$ .............................................. C12Q 1/48
[52] U.S. Cl. ...................................... 435/15; 435/16; 435/26; 435/805; 435/810
[58] Field of Search ....................... 435/14, 15, 16, 25, 435/26, 805, 810; 424/2; 422/61

[56] References Cited

U.S. PATENT DOCUMENTS

| | | | |
|---|---|---|---|
| 3,573,171 | 3/1971 | Green | 435/26 |
| 3,703,591 | 11/1972 | Bucolo | 435/10 |
| 3,867,259 | 2/1975 | Forgione | 435/26 |
| 3,929,580 | 12/1975 | Forgione | 435/26 |
| 4,006,061 | 2/1977 | Weeks | 435/26 |
| 4,035,239 | 7/1977 | McCloskey | 435/26 |
| 4,036,697 | 7/1977 | Pierre | 435/15 |
| 4,042,462 | 8/1977 | Johnson | 435/26 |

OTHER PUBLICATIONS

Methods of Enzymatic Analysis, Bergmeyer, 1974, Verlag Chemie Weinheim, pp. 509, 1509, 1690.
Wilkenson, "The Pathway of the Adaptive Fermentation of Galactose by Yeast", Biochem. J., 44, 1949, pp. 460–467.
Greengard, "Determination of Intermediary Metabolites by Enzymatic Fluorimetry", Nature, 178, (1956) pp. 632–637.
Kornberg, Methods of Enzymology, vol. 2, 1955, pp. 497–501.
Huzar, "Homologous Methylated and Nonmethylated Histidine Peptides in Skeletal and Cardiac Myosins", J. Biogical Chemistry, vol. 247, No. 3, 1972, pp. 745–753.
Bucher, "Uber ein Phosphatubertragendes Garungsferment", Biochimica et Biophysica Acta, vol. 1 (1947) pp. 292–314.
DeLey, "The Metabolism of D-Galactose in *Pseudomonas saccharophila*", Journal of Biological Chemistry, vol. 227, 1957, pp. 745–757.
Atkinson, Bio Chem. J., vol. 78, pp. 813–820, "Equilibrium Constant of Phosphryl Transfer", (1961).

*Primary Examiner*—Ernest G. Therkorn
*Attorney, Agent, or Firm*—Felfe & Lynch

[57] ABSTRACT

In a method for the quantative enzymatic determination of adenosine diphosphate (ADP) in aqueous solution by phosphorylation of the ADP with a kinase in the presence of a phosphorylated substrate therefor, with the formation of ATP and a dephosphorylated substrate, such as galactose, formate, pyruvate or nucleoside diphosphate, the dephosphorylated substrate is reacted, optionally with the insertion of a further adjuvant reaction, such as a decarboxylation, transamination or hexosidiation, with NAD(P) in the presence of a dehydrogenase and the NAD(P)H formed is either measured directly or reacted with a tetrazolium salt in the presence of an electron carrier, with the formation of a formazane, which latter is then measured.

A reagent suitable for carrying out this method contains a kinase, a phosphorylated substrate therefor different from ADP, a specific dehydrogenase for the dephosphorylated form of the substrate or for a transaminated, decarboxylated or hexosidized secondary product thereof, the co-enzyme of the dehydrogenase and a buffer, as well as optionally a tetrazolium salt, an electron carrier suitable therefor and optionally a surface-active agent.

5 Claims, No Drawings

METHOD FOR THE QUANTITATIVE ENZYMATIC DETERMINATION OF ADP

This application is a continuation of application Ser. No. 614,372, filed May 24, 1984, now abandoned, which, in turn is a continuation of application Ser. No. 059,366, filed Jul. 20, 1979, now abandoned.

The present invention is concerned with a method for the quantitative enzymatic determination (ADP adenosine diphosphate) soluble in water.

There has long been great interest in the field of biochemistry in the measurement of ADP and in the measurement of reactions yielding ADP. ADP formation is a measure for adenosing triphosphate conversion and thus for the utilization of the central energy carrier of the organism. However, the measurement of ADP is also of great importance in chemistry when heart, liver and kidney diseases are to be diagnosed. The detection of ADP in the course of reactions giving rise to ADP is also of great importance in biochemistry and in clinical chemistry. By way of example, there may here be mentioned the detection of pyruvate kinase and of creatine kinase forenzyme determinations and the detection of creatinine and glycerol for metabolite determinations.

Therefore, the determination of ADP in biological fluids, such as sera, in tissues, in bacteria-contaminated aqueousmaterials and in other aqueous fluids, is of great practical importance.

Three different procedures have been used for the enzymatic determination of ADP. The first depends upon the phosphorylation of ADP to ATP with phosphoenol pyruvate (PEP) and pyruvate kinase (PK) and detection of the resultant pyruvate with NADH/LDH (lactate dehydrogenase):

A
1. ADP + PEP $\xrightarrow{PK}$ ATP + pyruvate 2. pyruvate + NADH + H$^+$ $\xrightarrow{LDH}$ lactate + NAD$^+$ This process has been known for a long time and is described in Nature, 178, 632 (1956).

The other two procedures also depend upon the phosphorylation of ADP, for example, with creatine phosphate and creatine kinase (CK) and the detection of the ATP formed:

B
1. phosphoglyceraldehyde + NAD + phosphate $\xrightarrow{GADPH}$ 1,3-diphosphoglycerate + NAOH + H +

2. 1,3-diphosphoglycerate + ADP $\xrightarrow{PGK}$ 3-phosphoglycerate + ATP

PGK = phoaphoglycerol kinase
GAP-DH = glyceraldehyde phosphate dehydrogenase

This reaction has also been known for a long time and is described in BBA, 1, 292 (1947).

C
1. ADP + creatine phosphate $\xrightarrow{CK}$ ATP + creatine

2. ATP + glucose $\xrightarrow{HK}$ G-6-P + ADP 3. glucose-6-phosphate + NAD$^+$ $\xrightarrow{G-6-PDH}$ gluconate-6-phaosphate + NADH + H$^-$ HK = hexokinase
G-6-PDH = glucose-6-phosphate dehydrogenase This reaction has been used at least since 1955 and is described, for example, in A. Kornberg, Methods of Enzym., 2, 497 (1955).

However, these known methods suffer from various disadvantages which make their use difficult or expensive. Admittedly, the detection according to A is, in principle, suitable to serve as an indicator system for reactions which give ADP from ATP and has been used for this purpose; but what is measured as the decrease in NADH extinction. In such tests, for measurement-technical reasons, only a limited initial extinction of NADH can be present. The result of this is that theindicator enzyme LADH here used is not saturated with its substrate NADH and, consequently, does not achieve its maximum reaction rate. This must be compensated for by an increased use of enzyme. However, this is not only uneconomical but also entails the danger that other interfereing enzyme activities are introduced into the test system in comparatively large amounts. A further disadvantage results from the fact that, while high ADP concentrations the NADH may already have been consumed before complete conversion has occurred. The result is that the measured values are lower than they should be.

A serious disadvantage of method B is that while according to the principle of the preliminary indicator reaction a definite amount of ADP brings about a stoichiometrically calculable formation of NADH, but integral stoichiometry is not present and, therefore, the calculation is very complicated. Furthermore, the presence of ATP brings about an additional displacement of the equilibrium, which makes the calculation even more difficult. Therefore, this method has scarcely been used in practice. An amplification furthermore, of the measurement signal by a subsequent formazane reaction is not possible.

Method C does not possess these disadvantages. However, there are two other disadvantages which have to be taken into account. Since method C is based upon the phosphorylation of ADP to ATP and this ATP is then detected, it is obvious that this method is not suitable for the detection of ADP formed from ATP in a coupled test. As already mentioned, there is, however, a great interest in being able to measure many reactions which give ADP from ATP. However, it is desirable to always use the same indicator system for these detections because the required enzymes and reagents can be produced the more economically the larger the production batches can be made. On the other hand, it is, in principle, disadvantageous to carry our measurements in UV light because measurement devices for measurement in UV light are always substantially more expensive and complex than measurement devices for measurement in visible light.

Therefore, it is an object of the present invention to provide a method for the determination of ADP which does not suffer from the disadvantages of the known procedures. In particular, it is an object of the present invention to provide such a method which only requires short measurement times and only one incubation, which measures the absorption increase or, in the case of enzyme determinations, the absorption increase per minute, permits a measurement in visible light in order that simpler photometric devices can be used and, at the same time, can be coupled to various reactions which give ADP from ATP.

Thus, according to the present invention, there is provided a method for the quantitative enzymatic determination of adenosine diphosphate (ADP) in aqueous solution by phosphorylation with a kinase in the presence of a phosphorylating substrate thereof, with the formation of ATP and dephosphorylated substrate, which is characterised in that the dephosphorylated substrate, optionally with the insertion of a further adjuvant reaction, is reacted with NAD(P) in the presence of a dehydrogenase and the NAD(P)H formed measured directly or reacted with a tetrazolium salt in the presence of an electron carrier, with the formation of a formazane, which latter is then measured.

Thus, the basic principle of the method according to the present invention consists in coupling, not as heretofore with a reaction in which the NADH is consumed but rather with a reaction in which NAD or NADP is reduced to NADH and NADPH, respectively. Several embodiments of the method according to the present invention are possible since a number of different reactions of this type have been found to be adapted to be coupled with quantitative reaction courses.

However, it is not possible in every case to react the phosphorus-free substrate of the first reaction, in which ADP is phosphorylated, directly to ATP with the NAD or NADP and a dehydrogenase. In such cases, an adjuvant reaction must be introduced, in particular a decarboxylation reaction, a transamination reaction, or coupling with a hexose or pentose.

Moreover it is sometimes preferable not to measure directly the NAP(P) formed but to convert it to a dye in that an appropriate tetrazolium salt is converted in the presence of an electron carrier, for example diaphorase, to the corresponding formazane dye whereafter the resultant coloration is measured. Appropriate tetrazolium salts and electron carriers are known to those skilled in the art. Merely by way of example, mention may be made of 3-(4,5-dimethylthiazolyl-2)-2,5-diphenyltetrazolium bromide, notro blue tetrazolium chloride and 2-(p-iodophenyl)-3-(p-nitrophenyl)-5-phenyl-tetrazolium chloride.

According to a preferred embodiment of the method according to the present invention, this is carried out with galactose kinase and galactose dehydrogenase in the reaction sequence illustrated by the following equations:

1. Gal-1-P + ADP 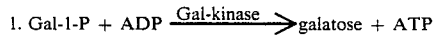 galatose + ATP 2. glactose + NAD+ 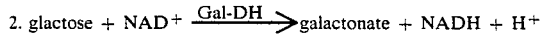 galactonate + NADH + H+

Gal-1-P = galactose-1-phosphate
Gal-kinase = galactose kinase
Gal-DH = galactose dehydrogenase These equations have already been known for a long time from Biochem. J., 44, 460 (1949) and J. Biol. Chem., 227, 745 (1957).

However, we have, surprisingly, now found that it is possible to couple these reaction with one another and with reactions which form ADP from ATP. In this way, the absorption increase due to the NADH formed becomes the measure of the amount of ADP or if, in the case of the coupled reactions which form ADP from ATP, enzyme activities are to be measured, the absorption increase per unit time due to the NADH formed becomes the measure for the enzyme activity to be determined. Hitherto, such a coupling was not deemed to be possible which follows merely from the fact that, for more than 20 years, a search has been made for a satisfactory process for the determination of ADP and the reactions have been known for such a long time.

According to an especially advantageous embodiment of this embodiment of the process according to the present invention, a further reaction is subsequently carried out which, with a tetrazolium salt in the presence of an electron carrier, leads to the reoxidation of the NADH formed, with the simultaneous formation of a coloured formazane which can easily be measured in the visible light. In a preferred ambodimental form, this corresponds to the following equation:

1. NADH + MTT+ 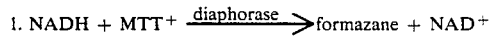 formazane + NAD+

MTT = 3-(4,5-dimethylthiazolyl-2(-2,5-diphenyl-tetrazolium bromide.

As electron carrier, it is preferred to use the above-mentioned diaphorase. However, other known electron carriers can also be employed. Thus, for example, phenazine methosulphate (PMS) and phenathroline methosulphate have proved to be very suitable.

The tetrazolium salt used is preferably the already mentioned MTT. However, other tetrazolium salts can also be employed. Good results have, in particular, also been obtained with nitro blue tetrazolium chloride (NBT) and 2-(p-iodophenyl)-3-(p-nitrophenyl)-5-phenyl-tetrazolium chloride (INT). The tetrazolium salt used is selected with due regard to the solubility of the formazane dye formed. Thus, if the latter has only a low solubility, then, in the case of high ADP concentrations, precipitation of the dye can take place which gives rise to measurement difficulties. For this reason, in the case of carrying out the process according to the present invention with the measurement of a formazane dye, it is preferable to add a surface-active agent which improves the solubility behaviour of the dye. Examples of surface-active agents which can be used include desoxycholic acid, saponin, alkylaryl-polyethylene glycol esters and ethers, sorbitol esters, such as sorbimacrogol oleate, polyethylene glycol lauryl ether and the like. In general, the concentration of the surface-active agent is from 0.3 to 3% in the test.

Admissible variations:

The nature of the buffer is not critical. Examples of buffers which can be used include tris, tra, imidazole, succinate, glycine and glycylglycine buffers. The buffer strength can be from 0.005 to 0.5 mol/l. and the pH value from 6 to 10.5.

Gal kinase 0.1 to 20 U/ml.
Gal-DH 0.05 to 20 U/ml.

The other embodiments of the process according to the present invention which are described hereinafter can also be coupled with the formazane formation. In the case of some of these reactions, this coupling is even to be preferred for equilibrium reasons. Further embodiments are described in the following:

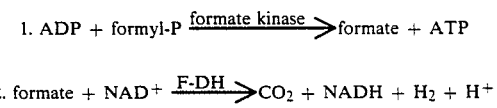

E

1. ADP + formyl-P $\xrightarrow{\text{formate kinase}}$ formate + ATP 2. formate + NAD$^+$ $\xrightarrow{\text{F-DH}}$ CO$_2$ + NADH + H$_2$ + H$^+$ F-DH = formate dehydrogenase Admissible variations:

For the buffer and buffer strength, the remarks made with regard to D again apply.
pH 6.0 to 10.0
formate kinase 0.05 to 50 U/ml.
formate-DH 0.1 to 100 U/ml.

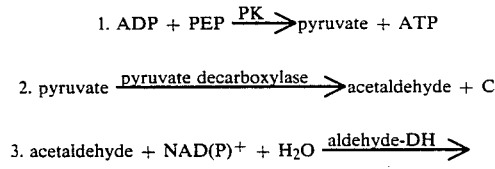

F

1. ADP + PEP $\xrightarrow{\text{PK}}$ pyruvate + ATP 2. pyruvate $\xrightarrow{\text{pyruvate decarboxylase}}$ acetaldehyde + CO$_2$ 3. acetaldehyde + NAD(P)$^+$ + H$_2$O $\xrightarrow{\text{aldehyde-DH}}$ acetate + NAD(P)H + H$^+$ Admissible variations The remarks made in D again apply with regard to the nature and strength of the buffer.
pH 4.5 to 7.5
pK 0.05 to 50 U/ml.
Al-DH 0.05 to 50 U/ml.
Pyr-DC 0.05 to 50 U/ml.

The following embodiment of the process according to the present invention is especially preferred:

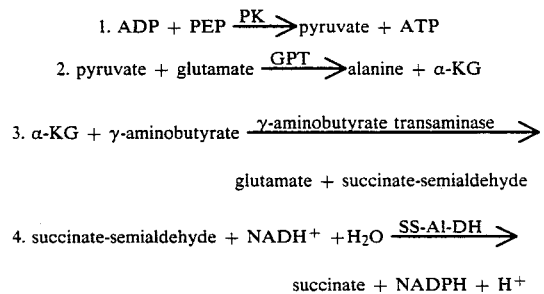

G

1. ADP + PEP $\xrightarrow{\text{PK}}$ pyruvate + ATP 2. pyruvate + glutamate $\xrightarrow{\text{GPT}}$ alanine + α-KG 3. α-KG + γ-aminobutyrate $\xrightarrow{\text{γ-aminobutyrate transaminase}}$ glutamate + succinate-semialdehyde 4. succinate-semialdehyde + NADH$^+$ + H$_2$O $\xrightarrow{\text{SS-Al-DH}}$ succinate + NADPH + H$^+$ GPT = glutamate-pyruvate transaminase
α-KG = α-ketoglutarate
SS-Al-DH = succinate-semialdehyde-dehydrogenase Admissible variations The remarks made in D apply with regard to the buffer and buffer strength.
pH 6.0 to 10.5
PK, GPT, GAB-GT, SS-Al-DH in each case 0.05 to 50 U/ml.

The following embodiment of the process according to the present invention is also especially preferred:

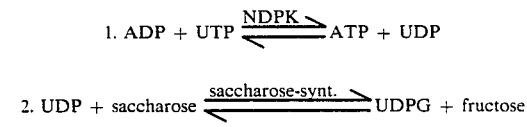

H

1. ADP + UTP $\xrightleftharpoons{\text{NDPK}}$ ATP + UDP

2. UDP + saccharose $\xrightleftharpoons{\text{saccharose-synt.}}$ UDPG + fructose

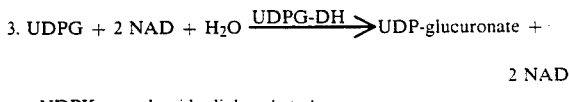

3. UDPG + 2 NAD + H$_2$O $\xrightarrow{\text{UDPG-DH}}$ UDP-glucuronate + 2 NAD nNDPK = nucleoside diphosphate kinase Admissible variations The remarks made in D again apply with regard to the nature and strength of the buffer
pH range 6 to 10.5
UDPG-DH 0.01 to 15 U/ml.
NDPK 1 to 50 U/ml.
saccharose synt. 0.05 to 10 U/ml.

The details for the carrying out of these embodiments are given in the following Examples, which explain these embodiments in more detail.

As already mentioned, the use of the present invention is especially advantageous for reactions in which ADP is formed from ATP. Therefore, in the following Table, there are given examples of enzymes and substrates in which the ADP to be measured is formed from ATP and for which the present invention can be applied. As explained in more detail in the following Examples, here, too, coupled reactions can be carried out. Not only the enzyme but also the stated substrate can be determined by the method according to the present invention. Which embodiment of the method according to the present invention is to be used in each particular case is essentially independent of the reaction to be detected.

TABLE 1

| enzyme | EC No. | substrate |
|---|---|---|
| hexokinase | 2.7.1.1 | ATP/hexoses |
| glucokinase | 2.7.1.2 | ATP/glucose |
| fructokinase | 2.7.1.4 | ATP/fructose |
| galactokinase | 2.7.1.6 | ATP/galactose |
| mannokinase | 2.7.1.7 | ATP/mannose |
| glucosamine kinase | 2.7.1.8 | ATP/2-amino-2-desoxy-D-glucose |
| phosphoglucokinase | 2.7.1.10 | ATP/lucose-1-P |
| phosphofructokinase | 2.7.1.11 | ATP/fructose-6-P |
| gluconokinase | 2.7.1.12 | ATP/D-gluconate |
| adenosine-kinase | 2.7.1.20 | ATP/adenosine |
| NAD-kinase | 2.7.1.23 | ATP/NAD |
| glycerol kinase | 2.7.1.30 | ATP/glycerol |
| glycerate kinase | 2.7.1.31 | ATP/glycerate |
| choline kinase | 2.7.1.32 | ATP/choline |
| pyruvate kinase | 2.7.1.40 | ATP/pyruvate |
| glucuronokinase | 2.7.1.43 | ATP/glucuronate |
| galacturonokinase | 2.7.1.44 | ATP/galacturonate |
| arabinokinase | 2.7.1.54 | ATP/arabinose |
| mannitol kinase | 2.7.1.57 | ATP/mannitol |
| inosine kinase | 2.7.1.73 | ATP/inosine |
| acetate kinase | 2.7.2.1 | ATP/acetate |
| carbamate kinase | 2.7.2.2 | ATP/NH$_3$/CO$_2$ |
| aspartate kinase | 2.7.2.4 | ATP/aspartate |
| carbamoyl phosphate synthase | 2.7.2.5 | 2 ATP/NH$_3$/CO$_2$/H$_2$O |
| formate kinase | 2.7.2.6 | ATP/formate |
| carbamoyl phosphate synthase | 2.7.2.9 | 2 ATP/glutamine/CO$_2$/H$_2$O |
| guanidinoacetate kinase | 2.7.3.1 | ATP/guanidine acetate |
| creatine kinase | 2.7.3.2 | ATP/creatine |
| arginine kinase | 2.7.3.3 | ATP/L-arginine |
| ammonia kinase | 2.7.3.8 | ATP/NH$_3$ |
| polyphosphate kinase | 2.7.4.1 | ATP (phosphate)n |
| adenylate kinase | 2.7.4.3 | ATP/AMP |
| nucleoside monophosphate kinase | 2.7.4.4 | ATP/nucleoside monophosphate |

TABLE 1-continued

| enzyme | EC No. | substrate |
|---|---|---|
| nucleoside di-phosphate kinase | 2.7.4.5 | ATP/nucleoside diphosphate |
| guanylate kinase | 2.7.4.6 | ATP/GMP |
| cytidylate kinase | 2.7.4.14 | ATP/CMP |
| succinyl-CoA-synthetase | 6.2.1.5 | ATP/succinate/CoA |
| glutaryl-CoA-synthetase | 6.2.1.6 | ATP/glutarate/CoA |
| malyl-CoA-synthetase | 6.2.1.9 | ATP/malate/CoA |
| glutamine synthetase | 6.3.1.2 | ATP/glutamate/$NH_3$ |
| asparagine synthetase | 6.3.1.4 | ATP/aspartate/$NH_3$ |
| γ-glutamyl-cysteine synthetase | 6.3.2.2 | ATP/glutamate/cysteine |
| glutathione synthetase | 6.3.2.3 | ATP/γ-glutamyl-cysteine/glycine |
| D-alanylalanine synthetase | 6.3.2.4 | ATP/2 D-alanine |
| urea carboxylase | 6.3.4.6 | ATP/urea/$CO_2$ |
| pyruvate carboxylase | 6.4.1.1 | ATP/pyruvate/$H_2O$/$CO_2$ |
| 5'-nucleosidase | 3.1.3.5 | ATP/ASN/$NH_3$/glutamate |
| adenosine desaminase | 3.5.4.4 | ATP/ASN/ISN/$NH_3$/glutamate |

The present invention also provides a reagent for the determination of ADP, which reagent comprises a kinase, a phosphorylated substrate therefor which is different from ADP and buffer, which is characterised in that it contains a dehydrogenase specific for the dephosphorylated form of this substrate or for a transaminated, decarboxylated or hexosidised secondary product thereof, as well as the coenzyme of the dehydrogenase.

In addition, this reagent can also contain a tetrazolium salt and an electron carrier suitable therefor, as well as optionally a surface-active agent and/or a system for the formation of ADP from ATP, as well as the salts needed for the particular enzymes used.

The system for the formation of ADP from ATP either comprises ATP and the kinase which is substance-specific for the particular ADP formation to be determined or, if it is to be used for the activity determination of this kinase, comprises ATP and the second substrate of the kinase.

The reagent according to the invention can be in dry, lyophilised form or in the form of an aqueous solution which is ready to use. In one particular embodiment, the reagent according to the present invention can be impregnated on to an appropriate carrier or can be incorporated into a test strip.

In the following Examples, the following abbreviations are used:

| Al-DH | aldehyde dehydrogenase |
|---|---|
| formate-DH | formate dehydrogenase |
| GPT | glutamate-pyruvate transaminase |
| GAB-GT | γ-aminobutyrate-α-ketoglutarate transaminase |
| SS-Al-DH | succinate-semialdehyde dehydrogenase |
| GOT | glutamate-oxalacetate transaminase |
| NDPK | nucleoside-5'-diphosphate kinase |
| UTP | uridine-5'-triphosphate |
| ADP | adenosine-5'-diphosphate |
| ATP | adenosine-5'-triphosphate |
| PEP | phosphoenol pyruvate |
| PK | pyruvate kinase |
| NAD | nicotinamide-adenine-dinucleotide |
| NADH | nicotinamide-adenine-dinucleotide, reduced |
| NADP | Nicotinamide-adenine-dinucleotide phosphate |
| NADPH | nicotinamide-adenine-dinucleotide phosphate, reduced |
| CK | creatine kinase |
| MTT | 3-(4,5-dimethylthiazolyl-2)-2,5-diphenyl-tetrazolium bromide |
| Gal-1-P | D-galactose-1-phosphate |
| Gal-kinase | galactose kinase |
| Gal-DH | galactose dehydrogenase |
| UDPG-DH | uridine-5'-phosphoglucose dehydrogenase |
| Pyr-DC | pyruvate decarboxylase |
| ADA | adenosine desamidase |

The following Examples are given for the purpose of illustrating the present invention:

EXAMPLE 1.

Determination of ADP with Gal-kinase, with the formation of NADH.

Temperature 25° C., measurement wavelength 365 nm, 1 cm. cuvette, test volume 2.02 ml.

| starting solution | sample (ml.) | blank (ml.) | concentration in the test |
|---|---|---|---|
| K phosphate buffer, pH 7.5, 0.1 mol/l | 0.2 | 0.2 | 10 mMol/l. |
| $MgCl_2$, 0.1 mol/l. | 0.2 | 0.2 | 10 mMol/l. |
| Gal-1-P, 60 mMol/l. | 0.1 | 0.1 | 3 mMol/l. |
| NAD, 40 mMol/l. | 0.1 | 0.1 | 2 mMol/l. |
| Gal-knase, 100 U/ml. | 0.1 | 0 1 | 5 U/ml. |
| Gal-DH, 12.5 U/ml. | 0.1 | 0.1 | 0.625 U/ml. |
| water | 1.2 | 1.2 | — |
| mix and then start with: | | | |
| ADP solution | 0.02 | | | mix, incubate, after cessation of the increase of the extinction, measure the extinction of the sample against the extinction of the blank. From the difference, there is obtained the ADP content of the sample according to the following equation:

$$\text{ADP (mMol/l.)} = \Delta E \times 29.71$$

EXAMPLE 2.

Determination of ADP with PK/pyruvate-DC, with the formation of NADH.

Temperature 25° C., measurement wavelength 365 nm, test volume 2 ml., 1 cm. cuvette

| starting solution | sample (ml.) | blank (ml.) | concentration in the test |
|---|---|---|---|
| imidazole buffer, pH 6.5, 0.2 mMol/l. | 1.0 | 1.0 | 0.1 mMol/l. |
| $MgSO_4$, 0.2 mMol/l. | 0.1 | 0.1 | 10 mMol/l. |
| NAD, 40 mMol/l. | 0.1 | 0.1 | 2 mMol/l. |
| PEP, 10 mMol/l. | 0.1 | 0.1 | 0.5 mMol/l. |
| Pyr-DC/PK/$A_1$-DH, 100 U/ml. of each | 0.05 | 0.05 | 2.5 U/ml. in each case |
| water | 0.65 | 0.65 | — |
| mix and then start with | | | |
| ADP | 0.02 | — | — | mix, incubate, after cessation of the increase of the extinction, measure the sample extinction against the extinction of the blank and then calculate the ADP content of the sample according to the following equation:

ADP (mMol/l.) = $\Delta E \times 29.71$

EXAMPLE 3.

Determination of ADP with formate kinase, with the formation of NADH.

Measurement temperature 25° C., measurement wavelength 365 nm., 1 cm. cuvette, test volume 2.02 ml.

| concentration of the starting solution | sample (ml.) | blank (ml.) | concentration in the test |
|---|---|---|---|
| dimethyl glutarate pH 6.9, 0.1 mMol/l. | 1.0 | 1.0 | 50 mMol/l. |
| formyl phosphate, 0.1 mMol/l. | 0.1 | 0.1 | 5 mMol/l. |
| formate kinase, 20 U/ml. | 0.1 | 0.1 | 1 U/ml. |
| formate-DH. 200 U/ml. | 0.1 | 0.1 | 10 U/ml. |
| NAD, 0.08 mMol/l. | 0.1 | 0.1 | 4 mMol/l. |
| MnSO$_4$, 0.1 mMol/l. | 0.1 | 0.1 | 5 mMol/l. |
| water | 0.5 | 0.5 | — |
| mix and then start with |  |  |  |
| ADP | 0.02 | — | — | mix, incubate, after cessation of the increase of the extinction, determine the extinction of the sample against the blank and calculate the content of ADP according to the following equation:

ADP (mMol/l.) = $\Delta E \times 29.71$

EXAMPLE 4.

Determination of ADP with GPT, GAB-GT and SS-Al-DH, with the formation of NADPH.

Measurement temperature 25° C., measurement wavelength 365 nm., 1 cm. cuvette, 2.22 ml. test volume.

| concentration of the starting solution | sample (ml.) | blank (ml.) | concentration in the test |
|---|---|---|---|
| imidazole buffer, pH 7.6, 0.1 mol/l. | 1.0 | 1.0 | 50 mMol/l. |
| MgSO$_4$, 100 mMol/l. | 0.1 | 0.1 | 1 mMol/l. |
| PEP, 20 mMol/l. | 0.1 | 0.1 | 1 mMol/l. |
| NADP, 20 mMol/l. | 0.1 | 0.1 | 1 mMol/l. |
| glutamate, 0.6 mol/l. | 0.2 | 0.2 | 60 mMol/l. |
| γ-aminobutyrate, 0.9 mol/l. | 0.2 | 0.2 | 90 mMol/l. |
| PK, 40 U/ml. | 0.1 | 0.1 | 2 U/ml. |
| GPT, 100 U/ml. | 0.1 | 0.1 | 5 U/ml. |
| GAB-GT, 50 U/ml. | 0.1 | 0.1 | 2.5 U/ml. |
| SS-Al-DH, 50 U/ml. | 0.1 | 0.1 | 2.5 U/ml. |
| mix, incubate, start with |  |  |  |
| ADP | 0.02 | — | — | mix, await cessation of the increase of the extinction and from the difference between the extinction of the sample and that of the blank, calculate the content of ADP according to the following equation:

ADP (mMol/l.) = $\Delta E \times 30.29$

EXAMPLE 5.

Determination of creatinine with the formation of formazane.

Measurement temperature 25° C., measurement wavelength 576 nm., 1 cm. cuvette, 2.5 ml. test volume.

| concentration of the starting solution | sample (ml.) | blank (ml.) | concentration in the test |
|---|---|---|---|
| glycine buffer cont. 5% "Triton" X100, 0.25 mol/l. pH 8.0 | 1.0 | 1.0 | 2% 0.1 mol/l. |
| NADP, 0.1 mol/l. | 0.05 | 0.05 | 2 mMol/l. |
| ATP, 0.05 mol/l. | 0.05 | 0.05 | 1 mMol/l. |
| PEP, 20 mMol/l. | 0.05 | 0.05 | 0.4 mMol/l. |
| glutamate, 50 mMol/l. | 0.05 | 0.05 | 1 mMol/l. |
| γ-aminobutyrate, 0.475 mol/l. | 0.5 | 0.5 | 95 mMol/l. |
| MgCl$_2$, 0.1 mol/l. | 0.05 | 0.05 | 2 mMol/l. |
| MTT, 1.5 mMol/l. | 0.5 | 0.5 | 0.3 mMol/l. |
| CK, 500 U/ml. |  |  | 10 U/ml. |
| PK, 200 U/ml. |  |  | 4 U/ml. |
| GPT, 200 U/ml. |  |  | 4 U/ml. |
| diaphorase, 25 U/ml. | 0.05 | 0.05 | 0.5 U/ml. |
| GAB-GT, 200 U/ml. |  |  | 4 U/ml. |
| SS-Al-DH, 200 U/ml. | 0.05 | 0.05 | 4 U/ml. |
| sample | 0.05 | — | — |
| mix and start with |  |  |  |
| creatininase, 500 U/ml. | 0.05 | 0.05 | 10 U/ml. | mix, incubate for 15 minutes and, at the end of the increase of the extinction, measure the extinction of the sample against that of the blank and calculate the creatinine content according to the following equation:

creatinine (mMol/l.) = $\Delta E \times 2.994$

The reaction conditions are fixed by the optimised creatinine determination. For the ADP determination according to the invention, there applies that stated in Example 4.

EXAMPLE 6.

Determination of CK, with the formation of NADPH,

Measurement temperature 25° C., measurement wavelength 365 nm., 1 cm. cuvette, 2.2 ml. test volume

| concentration of the starting solution | sample (ml.) | concentration in the test |
|---|---|---|
| glycine buffer, pH 9, 169 mMol/l. |  | 84.5 mMol/l. |
| creatine, 64 mMol/l. |  | 32 mMol/l. |
| NaCl | 1.1 | 76.5 mMol/l. |
| MgCl$_2$, 72.6 mMol/l. | 0.1 | 3.3 mMol/l. |
| ATP, 35.2 mMol/l. | 0.05 | 0.8 mMol/l. |
| PEP, 30.8 mMol/l. | 0.05 | 0.7 mMol/l. |
| NADP, 44 mMol/l. | 0.1 | 2 mMol/l. |
| glutamate, 44 mMol/l. | 0.05 | 1 mMol/l. |
| γ-aminobutyrate, 0.418 mol/l. | 0.5 | 95 mMol/l. |
| PK, 176 U/ml. |  | 4 U/ml. |
| GPT, 176 U/ml. |  | 4 U/ml. |
| GAB-GT, 176 U/ml. |  | 4 U/ml. |
| SS-Al-DH, 176 U/ml. | 0.05 | 4 U/ml. |
| sample | 0.2 |  | mix, incubate for 2 minutes and then read off Δ E at 1 minute intervals and calculate the amount of CK in the sample according to the following equation:

$$CK\ (U/ml.) = \Delta E/\min \times 3.143$$

The reaction conditions are fixed by the optimised creatine kinase determination. For the ADP determination according to the invention, there applies that stated in Example 4.

EXAMPLE 7.

Determination of ADP, with the formation of NADH.

Measurement temperature 25° C., measurement wavelength 365 nm., 1 cm. cuvette, test volume 1.6 ml.

| starting solution | ml. | end concentration in the test |
|---|---|---|
| glycylglycine, pH 8.0, 0.05 mMol/l. | 2.1 | 33.0 mMol/l. |
| NAD, 35 mMol/l. | 0.1 | 1.13 mMol/l. |
| saccharose, 500 mMol/l. | 0.5 | 78.1 mMol/l. |
| UDPG-DH, 3 U/ml. | 0.05 | 0.05 U/ml. |
| NDPK, 400 U/ml. | 0.05 | 6.25 U/ml. |
| UTP, 16.5 mMol/l. | 0.1 | 0.52 mMol/l. |
| saccharose synthetase. 12 U/ml. | 0.1 | 0.38 U/ml. |
| mix, pipette into microcuvettes | | |

| | blank (ml.) | sample (ml.) |
|---|---|---|
| mix | 1.5 | 1.5 |
| water | 0.1 | — |
| sample | — | 0.1 | mix, after cessation of the increase of the extinction, measure the extinction of the sample against that of the blank and calculate the ADP content according to the following equation:

$$ADP\ (mMol/l.) = \Delta E \times 2.353$$

Admissible variations:

nature and strength of the buffer: see Example 1, pH range 6.0–10.5; UDPG-DH 0.01–15 U/ml., NDPK 0.2–50 U/ml., saccharose synthetase 0.05–10 U/ml.

EXAMPLE 8.

Determination of creatinine with the formation of NADH.

Measurement temperature 25° C., measurement wavelength 365 nm., 1 cm. microcuvette, test volume 1.55 ml.

Preperation of reagent mixture:

| concentration of the starting solution | ml. | concentration in the test |
|---|---|---|
| glycylglycine, pH 8.0, 0.1 mMol/l. | 1.9 | 61 mMol/l. |
| NAD, 35 mMol/l. | 0.1 | 1.13 mMol/l. |
| saccharose, 0.5 mol/l. | 0.5 | 80.6 mMol/l. |
| UDPG-DH, 3 U/ml. | 0.05 | 0.05 U/ml. |
| NDPK, 400 U/ml. | 0.05 | 6.45 U/ml. |
| UTP, 16.5 mMol/l. | 0.1 | 0.53 mMol/l. |
| ATP, 16.7 mMol/l. | 0.1 | 0.54 mMol/l. |
| saccharose synthetase. 12 U/ml. | 0.1 | 0.38 U/ml. |
| CK, 500 U/ml. | 0.05 | 8 U/ml. |
| sample | 0.05 | |
| mix, pipette in microcuvettes | | |

| | blank (ml.) | sample (ml.) |
|---|---|---|
| mix | 1.5 | 1.5 |
| water | 0.05 | — |
| creatininase, 350 U/ml. | — | 0.05 |

After cessation of the increase of the extinction, measure the extinction of the sample against the extinction of the test blank and measure the creatinine content of the sample by calculation according to the following equation:

$$creatinine\ (mMol/l.) = E \times 9.12$$

The reaction conditions are fixed by the optimised creatinine determination. For the use of the ADP determination according to the present invention, there applies that stated in Example 7.

EXAMPLE 9.

Determination of ammonia, with the formation of NADH.

Measurement temperature 25° C., measurement wavelength 365 nm., 1 cm. microcuvette, test volume 1.6 ml. The enzymes used are to be substantially free from ammonium ions.

Preparation of reagent mixture:

| concentration of the starting solution | ml. | end concentration in the test |
|---|---|---|
| imidazole buffer, pH 7.8, 0.1 mol/l. | 1.5 | 47 mMol/l. |
| glutamic acid, 0.1 mol/l. | 0.2 | 6.2 mMol/l. |
| MgCl$_2$, 0.41 mol/l. | 0.1 | 12.8 mMol/l. |
| KCl, 0.26 mol/l. | 0.1 | 8.1 mMol/l. |
| NAD, 35 mMol/l. | 0.1 | 1.09 mMol/l. |
| saccharose, 0.5 mol/l. | 0.5 | 78.1 mMol/l. |
| UTP, 16.5 mMol/l. | 0.1 | 0.52 mMol/l. |
| ATP, 32.3 mMol/l. | 0.1 | 1.01 mMol/l. |
| glutamine synthetase, 3 U/ml. | 0.05 | 0.05 U/ml. |
| saccharose synthetase, 12 U/ml. | 0.1 | 0.38 U/ml. |
| NDPK, 400 U/ml. | 0.05 | 6.25 U/ml. |
| UDPG-DH, 3 U/ml. | 0.1 | 0.09 U/ml. |
| mix, pipette into microcuvettes | | |

| | blank (ml.) | sample (ml.) |
|---|---|---|
| mix | 1.5 | 1.5 |
| water | 0.1 | — |
| sample | — | 0.1 |

After cessation of the increase of the extinction, measure the extinction of the sample against that of the blank and calculate the ammonia content of the sample according to the following equation:

$$ammonia\ (mMol/l.) = \Delta E \times 2.253$$

Admissible variations:

nature and strength of the buffer: see Example 1; pH range 6.9–7.8; UDPG-DH 0.02–15 U/ml.; saccharose synthetase 0.1–10 U/ml.; NDPK 0.2–50 U/ml.; glutamine-synthetase 0.2–10 U/ml.

EXAMPLE 10.

Determination of ammonia, with the formation of NADH,

The determination can also be carried out with the help of carbamate kinase, for example, from *Streptococcus faecalis*.

Measurement temperature 37° C., measurement wavelength 365 nm., 1 cm. cuvette, test volume 1.6 ml.

Preparation of a reagent mixture:

| concentration of the starting solution | ml. | concentration in the test |
|---|---|---|
| imidazole buffer, pH 7.8, 0.1 mol/l. | 1.5 | 47 mMol/l. |
| potassium carbonate, 0.5 mol/l. | 0.2 | 31.2 mMol/l. |
| MgCl$_2$, 0.41 mol/l. | 0.1 | 12.8 mMol/l. |
| NAD, 35 mMol/l. | 0.1 | 1.09 mMol/l. |
| saccharose, 0.5 mol/l. | 0.5 | 78.1 mMol/l. |
| UTP, 15.6 mMol/l. | 0.1 | 0.52 mMol/l. |
| ATP, 32.3 mMol/l. | 0.1 | 1.01 mMol/l. |
| UDPG-DH, 3 U/ml. | 0.1 | 0.09 U/ml. |
| NDPK, 400 U/ml. | 0.05 | 6.25 U/ml. |
| saccharose synthetase, 12 U/ml. | 0.1 | 0.38 U/ml. |
| carbamate kinase, 100 U/ml. | 0.15 | 4.69 U/ml. | mix, pipette into microcuvettes

|  | blank (ml.) | sample (ml.) |
|---|---|---|
| mix | 1.5 | 1.5 |
| water | 0.1 | — |
| sample | — | 0.1 | leave to stand for about 20 minutes at 37° C.

After cessation of the increase of the extinction, measure the extinction of the sample against that of the blank and calculate the ammonia content according to the following equation:

$$\text{ammonia (mMol/l.)} = \Delta E \times 4.706.$$

EXAMPLE 11.

Determination of ammonia, with the formation of NADPH.

Measurement temperature 25° C., measurement wavelength 365 nm., 1 cm. cuvette, test volume 2.25 ml.

| concentration of the starting solution | sample (ml.) | blank (ml.) | concentration in the test |
|---|---|---|---|
| imidazole buffer, pH 7.0; 500 mMol/l. | 1.0 | 1.0 | 222 mMol/l. |
| KCl, 400 mMol/l. | 0.1 | 0.1 | 18 mMol/l. |
| MgCl$_2$, 800 mMol/l. | 0.1 | 0.1 | 35 mMol/l. |
| NADP, 20 mMol/l. | 0.1 | 0.1 | 0.9 mMol/l. |
| ATP, 32 mMol/l. | 0.1 | 0.1 | 1.4 mMol/l. |
| PEP, 20 mMol/l. | 0.1 | 0.1 | 0.9 mMol/l. |
| glutamate, 100 mMol/l. | 0.2 | 0.2 | 8.9 mMol/l. |
| ε-aminobutyrate, 900 mMol/l. | 0.2 | 0.2 | 80 mMol/l. |
| PK, 30 U/ml. | 0.1 | 0.1 | 1.3 U/ml. |
| GPT, 60 U/ml. |  |  | 2.7 U/ml. |
| GAB-GT, 60 U/ml. |  |  | 2.7 U/ml. |
| SS-DH, 50 U/ml. |  |  | 2.2 U/ml. |
| sample | 0.2 | — | — |
| water | — | 0.2 | — | mix, allow the pre-reaction to run to completion, start with

| | | | |
|---|---|---|---|
| glutamine synthetase, 10 U/ml. | 0.05 | 0.05 | 0.2 U/ml. | mix, incubate for about 20 minutes and at the end of the increase of the extinction, determine the extinction of the sample against that of the blank and calculate the ammonia content according to the following equation:

$$\text{ammonia (mMol/l.)} = \Delta E \times 3.214$$

Admissible variations:

nature and strength of the buffer: phosphate, succinate and imidazole buffer and possibly also Tris and Tra buffer: pH 6.8–7.8; PK, GPT, GAB-GT, SS-DH in each case 0.05–50 U/ml.; glutamine synthetase 0.02–10 U/ml.

EXAMPLE 12.

Determination of 5'-nucleotidase, with the formation of NADPH.

Measurement temperature 25° C., measurement wavelength 365 nm., 1 cm. cuvette, test volume 2.25 ml.

| concentration of the starting solution | sample (ml.) | blank (ml.) | concentration in the test |
|---|---|---|---|
| K phosphate buffer, pH 7.2, 100 mMol/l. | 1.0 | 1.0 | 444 mMol/l. |
| KCl, 400 mMol/l. | 0.1 | 0.1 | 18 mMol/l. |
| MgCl$_2$, 800 mMol/l. | 0.1 | 0.1 | 35 mMol/l. |
| NADP, 2 mMol/l. | 0.1 | 0.1 | 0.9 mMol/l. |
| ATP, 32 mMol/l. | 0.1 | 0.1 | 1.4 mMol/l. |
| PEP, 20 mMol/l. | 0.1 | 0.1 | 0.9 mMol/l. |
| glutamate, 100 mMol/l. | 0.2 | 0.2 | 8.9 mMol/l. |
| γ-aminobutyrate, 900 mMol/l. | 0.2 | 0.2 | 80 mMol/l. |
| β-glycerophosphate, 80 mMol/l. | 0.1 | 0.1 | 3.5 mMol/l. |
| PK, 30 U/ml. |  |  | 1.3 U/ml. |
| GPT, 60 U/ml. |  |  | 2.7 U/ml. |
| GAB-GT, 60 U/ml. |  |  | 2.7 U/ml. |
| SS-DH, 50 U/ml. |  |  | 2.2 U/ml. |
| ADA, 200 U/ml. |  |  | 8.8 U/ml. |
| sample | 0.1 | 0.1 |  | mix, incubate for about 10 minutes and then start with

| | | | |
|---|---|---|---|
| AMP, 80 mMol/l. | 0.05 | — | 1.8 mMol/l. |

The content of 5'-nucleotidase is calculated from the following equation:

$$\text{5'-nucleotidase (U/ml.)} = \Delta E/\text{min} \times 6.43$$

Permissible variations:

buffer: phosphate or succinate; pH 6.8–7.3; ADA: 1.2–20 U/ml.

We claim:

1. Method for quantitative enzymatic determination of adenosine diphosphate (ADP) formed from ATP in the presence of adenosine triphosphate (ATP) comprising contacting a sample containing ADP with a kinase and a phosphorylated substrate to form ATP from ADP and a dephosphorylated substrate, reacting said dephosphorylated substrate with NAD(P) in the presence of a dehydrogenase to form NAD(P)H, and measuring NAD(P)H as a measure of ADP originally present.

2. Method of claim 1, wherein said phosphorylated substrate is galactose-1-phosphate, formyl-phosphate, phosphoenol pyruvate, creatine phosphate, glucose-6-phosphate, or a nucleoside triphosphate.

3. Method of claim 1, further comprising reacting said dephosphorylated substrate in a further reaction.

4. Method of claim 3, wherein said further reaction is a decarboxylation, transamination, or hexosidation reaction.

5. Method of claim 1, further comprising reacting said NAD(P)H with a tetrazolium salt in the presence of an electron carrier to form formazone, and determining said formazone as a measure of initial ADP present.

* * * * *

UNITED STATES PATENT AND TRADEMARK OFFICE
CERTIFICATE OF CORRECTION

PATENT NO. : 4,923,796

DATED : May 8, 1990

INVENTOR(S) : Ulfert Deneke et al.

It is certified that error appears in the above-identified patent and that said Letters Patent is hereby corrected as shown below:

Column 1, line 53: "NAOH" should be -- NADH --;

line 57: "phoaphoglycerol" should be -- phosphoglycerol --.

Column 2, line 2: "6-phaosphate" should be -- 6-phosphate --.

Column 5, line 48: "NADH+" should be -- $NADP^+$ --.

Column 6, line 7: "nNDPK" should be -- NDPK --;

line 42: "lucose" should be -- glucose --.

Signed and Sealed this

Twenty-seventh Day of October, 1992

Attest:

DOUGLAS B. COMER

Attesting Officer      Acting Commissioner of Patents and Trademarks